United States Patent [19]

Betush

[11] Patent Number: 4,966,551
[45] Date of Patent: Oct. 30, 1990

[54] VACUUM EVACUATOR FOR DENTAL DEBRIS

[76] Inventor: Frank A. Betush, 375 Hargrave, Inglewood, Calif. 90302

[21] Appl. No.: 212,618

[22] Filed: Jun. 28, 1988

[51] Int. Cl.$^5$ .............................................. A61C 17/14
[52] U.S. Cl. ....................................... 433/95; 604/32; 433/126
[58] Field of Search ................... 433/95, 126; 604/119, 604/902, 32; 406/113, 151, 152, 153, 192

[56] References Cited

U.S. PATENT DOCUMENTS

| | | | |
|---|---|---|---|
| 811,111 | 1/1906 | Wegefarth | 604/32 |
| 3,232,578 | 2/1966 | Cousins | 433/95 |
| 3,517,669 | 6/1970 | Buono et al. | 604/119 |
| 3,780,736 | 12/1973 | Chen | 604/32 |
| 4,451,257 | 5/1984 | Atchley | 604/119 |
| 4,526,573 | 7/1985 | Lester et al. | 604/119 |
| 4,861,266 | 8/1989 | Ashiku | 433/95 |

Primary Examiner—John J. Wilson

[57] ABSTRACT

A long life vacuum for use primarily by a dental assistant for evacuating debris from the mouth of a patient during dental operations. The instrument takes the form of an open-ended tube having a quick disconnect coupler at one end to enable the tube to be coupled to a vacuum line. The other end of the tube is intended to be inserted into the mouth of the patient. The instrument is formed entirely of plastic so that it may be conveniently sterilized in a high temperature autoclave. Specifically, plastic seals are used instead of O-rings since O-rings are incapable of withstanding high temperatures and/or chemicals used during the sterilizing operations. In addition, there are no metal parts which would be subject to corrosive attach by the bonding materals currently used by many dentists. The instrument includes a valve which is operated by the dental assistant, and which is sealed to the tube by integral plastic seals.

3 Claims, 2 Drawing Sheets

VACUUM EVACUATOR FOR DENTAL DEBRIS

BACKGROUND OF THE INVENTION

Vacuum evacuators are commonly used by dental assistants during dental procedures to remove debris from the mouth of the patient. The evacuator usually takes the form of a hollow tube which is inserted into the patient's mouth, and which is coupled to a high vacuum line. This enables the instrument to remove the debris from the mouth during the dental procedures. An appropriate valve is provided in the prior art evacuator to enable the dental assistant to turn the instrument on and off.

A problem encountered with the prior art vacuum evacuators is that they are not susceptible to high temperature sterilization because of the O-rings used in the valves and couplers of the instrument, and also because they usually include metal parts which are susceptible to corrosive attack.

It is accordingly an objective of the present invention to provide an improved vacuum debris evacuator which is composed entirely of molded high temperature plastic, and which may conveniently be sterilized at high temperatures and/or by appropriate chemicals, and which does not contain any metal parts which would be subject to corrosive attack.

BRIEF DESCRIPTION OF THE DRAWINGS

FIG. 3A is a side elevation of a valve incorporated into the unit of FIG. 1;

FIG. 3B is an end view of the valve of FIG. 3A taken along the line 3B—3B;

FIG. 4A is a side view of a coupler used to couple the instrument of FIG. 1 to a vacuum line; and FIG. 4B is a side section of the coupler shown in FIG. 4A, taken along the line 4B—4B of FIG. 4A.

DETAILED DESCRIPTION OF THE ILLUSTRATED EMBODIMENT

Figure 1:
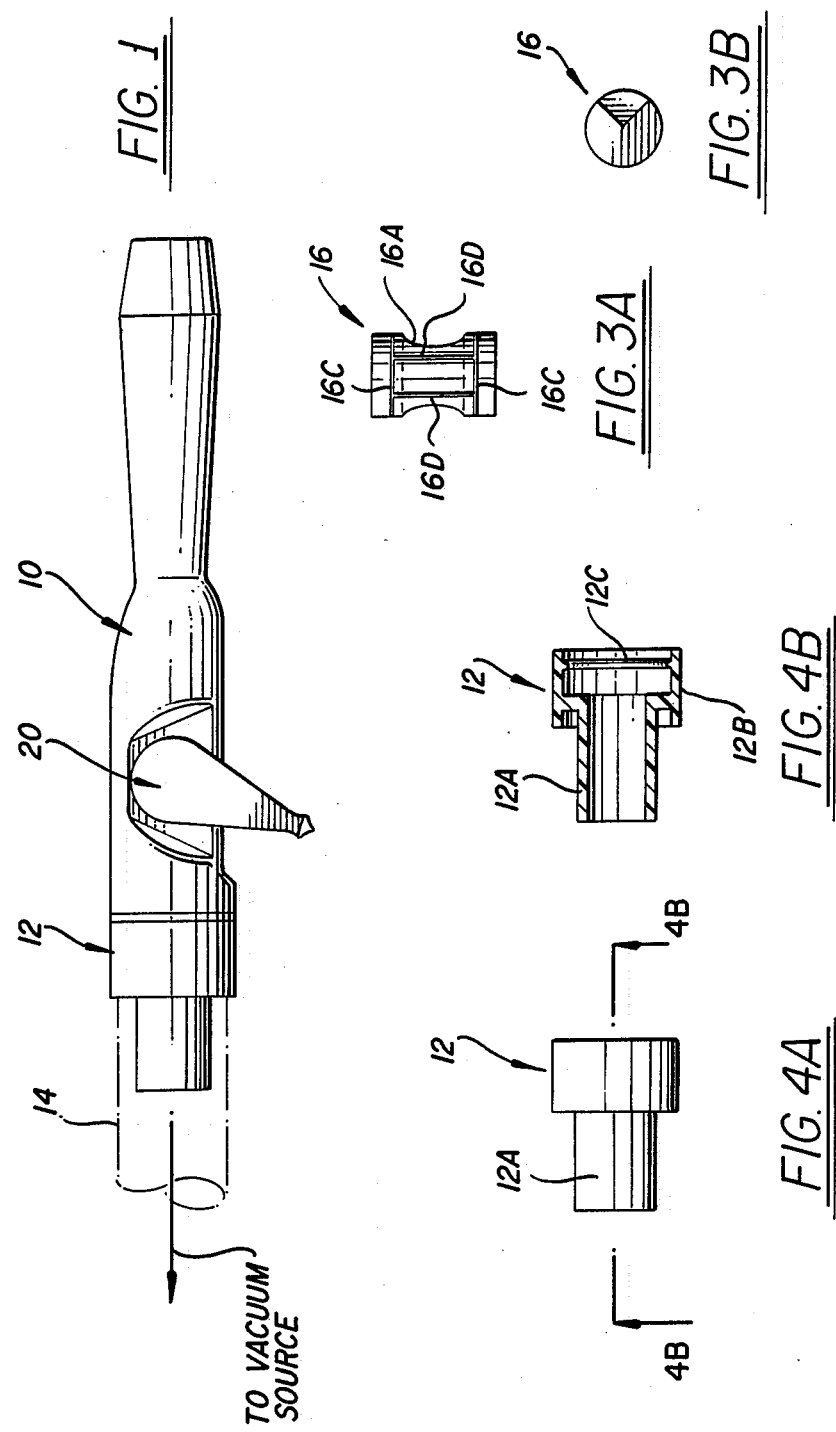
FIG. 1 is a side elevational view of a valved vacuum evacuator which may be constructed to incorporate the concepts of the invention.

The instrument shown in FIG. 1 includes an open ended hollow tubular member 10 having a longitudinal passage extending therethrough. A coupler 12 is plugged into one end of the tubular member 10 as a quick disconnect coupler, and it serves to couple the instrument to a line 14 which extends to an appropriate vacuum source.

The coupler 12 is shown in FIGS. 4A and 4B. As shown, it has a section 12A of reduced diameter for receiving the line, and a forward section 12B for receiving the end of the tubular member 10. The forward portion 12B has an internal groove 12C.

Figure 2:
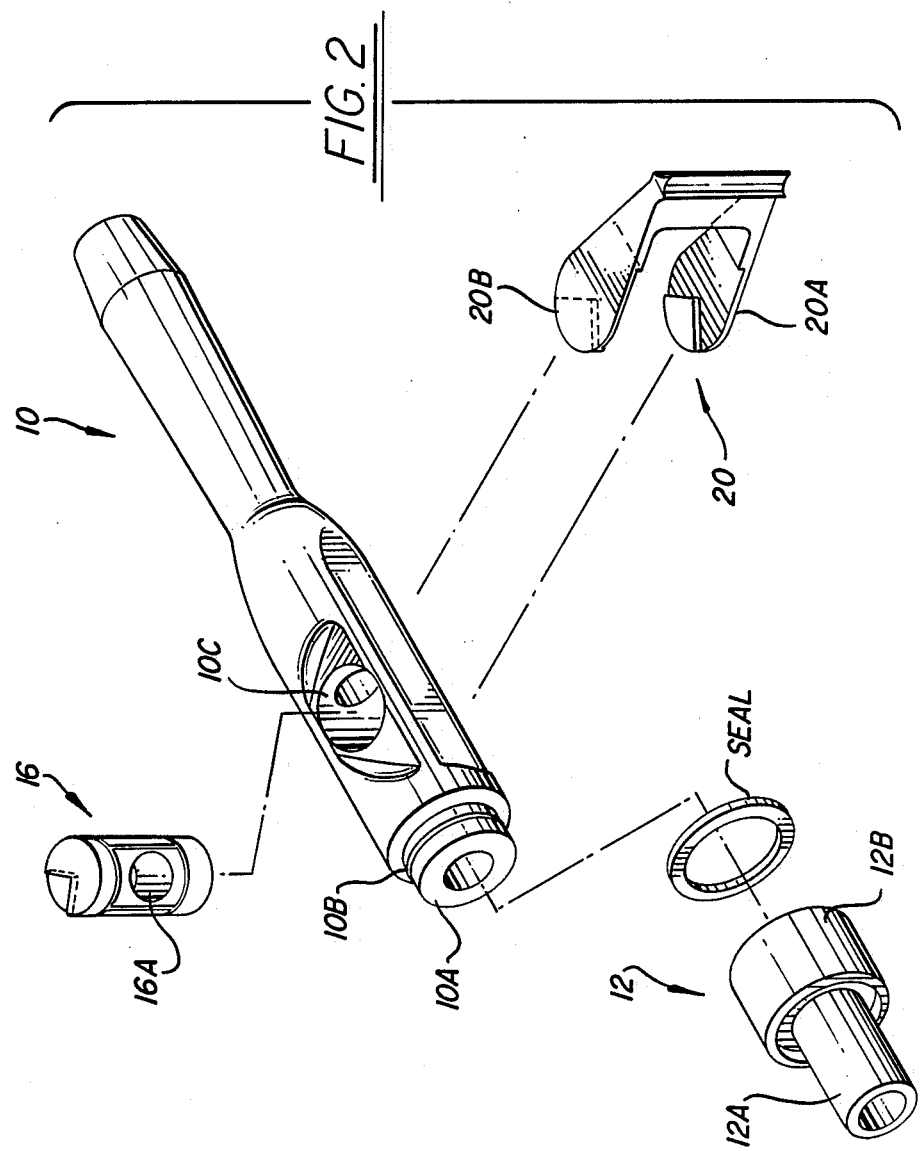
FIG. 2 is an exploded perspective view of the evacuator of FIG. 1.

As shown in FIG. 2, the tubular member 10 has an end 10A of reduced diameter which receives the end 12B of coupler 12. A circumferential ridge 10B is formed around the circumference of section 10A to be received in the groove 12C of the coupler to form a snap-fit quick disconnect coupling with the coupler and also to serve as a seal. An additional removable washer seal, as shown in FIG. 2, may also be used.

The tubular member is formed of high temperature plastic so that it may be sterilized at high temperatures, after it has been decoupled from the line 14 and from the coupler 12.

The tubular member 10 has a circular transverse opening 10C extending through it for receiving a solid cylindrical valve 16 which is shown in FIGS. 2, 3A and 3B. Valve 16 fits into the opening 10C to be positioned across the inner passage of tubular member 10.

The valve 16 has a transverse opening 16A extending through it, and it may be turned within the tubular member 10 to align the opening 16A with the internal passage of the tubular member so as to open the passage, and it may also be turned to a second angular position in which the opening 16A extends perpendicularly to the passage so as to close the passage. The valve 16 may also be turned to intermediate positions to control the flow of fluid through the passage.

The valve 16 is provided with a pair of circumferential integral ridges 16C on opposite ends of opening 16A, and it is also provided with integral ridges 16D on opposite sides of the opening 16A. The ridges 16C and 16D serve as seals between the valve member and the wall of the passage through the tubular member 10.

The valve 16, like the tubular member 10, is preferably formed of high temperature molded plastic material, so that the instrument may be sterilized at high temperatures with the valve in place.

The valve 16 is operated by a U-shaped handle 20 which has first and second arms 20A and 20B extending across the opposite sides of the tubular member 10 to engage the ends of the valve 16 which are exposed through the opening 10C in the tubular member. As shown, the inner faces of the ends of arms 20A and 20B are configured to interact with the configured ends of the valve 16 so that the handle 20 securely locks with and is coupled to the valve. Accordingly, when the handle 20 is turned from one position to another, the valve 16 is turned within the passage 10 between its open position and its closed position, or to any intermediate position for flow control.

Handle 20 is also preferably formed of high temperature molded plastic material, so that the instrument may be sterilized at high temperatures with the handle and valve in place. The handle is removable for cleaning and servicing, without the need for tools.

It will be appreciated that all seals within the sterilizable portion of the instrument are integral plastic seals, and no O-rings are used within the sterilizable portion. It should also be appreciated that there are no metal parts in the instrument which would be subject to corrosive chemical attack.

The invention provides, therefore, an improved vacuum evacuator for dental debris which is not subject to corrosive attack, and which may be repeatedly sterilized at high temperatures without any deterioration to the instrument.

While a particular embodiment of the invention has been shown and described, modifications may be made. It is intended in the claims to cover all modifications which come within the spirit and scope of the invention.

I claim:

1. A vacuum-type instrument comprising: an elongated open-ended tubular member having a longitudinal passage extending therethrough for drawing debris from the mouth of a patient during a dental procedure and having a second end for receiving a quick-disconnect coupler coupled to a line extending to a vacuum source, said second end having a circumferential ridge to be received in an internal groove in said coupler in a snap-fit relationship, said tubular member having a circular transverse opening therein; a solid cylindrical valve member received in the transverse opening in said tubular member and having a transverse port extending therethrough, said valve member being rotatable in said transverse opening between first and second angular positions to open and close the longitudinal passage through said tubular member said valve member having a pair of circumferential ridges formed on opposite ends of said transverse port and a pair of longitudinal ridges formed on opposite sides of said transverse port to provide seals between the surface of said valve member and the wall of said longitudinal passage; and a u-shaped handle positioned externally of said tubular member for turning said valve member and for retaining said valve member in said transverse opening, said handle having spaced-apart arms engaging the ends of said valve member, with the ends of said valve member and the inner surfaces of the ends of said arms being configured to interact with one another so as to couple the handle to the valve member.

2. The vacuum-type instrument set forth in claim 1, in which said tubular member, said valve member and said handle are all formed of high temperature plastic material so that the instrument may be sterilized at high temperatures after it has been decoupled from the coupler.

3. The vacuum-type instrument set forth in claim 1, in which the handle is removable from the valve member and the valve member is removable from the tubular member for cleaning and servicing purposes.

* * * * *